(12) United States Patent
Dongara et al.

(10) Patent No.: US 6,635,598 B2
(45) Date of Patent: Oct. 21, 2003

(54) STABLE AND SELECTIVE DEHYDROGENATION CATALYST AND A PROCESS FOR THE PREPARATION THEREOF

(75) Inventors: Rajeswer Dongara, District Vadodara (IN); Krishnamurthy Konda Ramaswamy, District Vadodara (IN)

(73) Assignee: Indian Petrochemicals Corporation Limited, Vadodara (IN)

( * ) Notice: Subject to any disclaimer, the term of this patent is extended or adjusted under 35 U.S.C. 154(b) by 0 days.

(21) Appl. No.: 09/832,187

(22) Filed: Apr. 10, 2001

(65) Prior Publication Data

US 2002/0022755 A1 Feb. 21, 2002

(30) Foreign Application Priority Data

Apr. 20, 2000 (IN) .................... 375/MUM/2000

(51) Int. Cl.$^7$ .................. B01J 27/06; B01J 27/128; B01J 27/138
(52) U.S. Cl. .............. 502/226; 502/224; 502/227; 502/229; 502/230; 502/231
(58) Field of Search .................. 502/224, 226, 502/227, 229, 230, 231

(56) References Cited

U.S. PATENT DOCUMENTS

| 3,950,270 | A | * | 4/1976 | Paynter et al. | |
| 4,136,064 | A | * | 1/1979 | Hayes et al. | |
| 4,197,416 | A | * | 4/1980 | Antos | 585/379 |
| 4,486,547 | A | * | 12/1984 | Imai et al. | 502/223 |
| 4,551,574 | A | * | 11/1985 | Imai et al. | 585/660 |
| 4,608,360 | A | * | 8/1986 | Abrevaya et al. | 502/226 |
| 5,677,260 | A | * | 10/1997 | Dongara et al. | 502/339 |

* cited by examiner

Primary Examiner—Elizabeth D. Wood
(74) Attorney, Agent, or Firm—Ladas & Parry

(57) ABSTRACT

A novel catalyst for use in dehydrogenation of saturated hydrocarbons to unsaturated hydrocarbons and a method for its preparation is disclosed. Said catalyst comprises a composite incorporated within its spatial geometry on a percentage by weight basis, with a uniform concentration gradient, the following active elements:

from 0.1 to 5.0% of a noble metal;
from 0.1 to 5.0% of a metal of Group IV A;
from 0.1 to 6.0% of a metal Group III A;
from 0.1 to 10.0% of an alkali or alkaline earth metal element;
from 0.01 to 10.0% of a halogen; and
from 0.1 to 5.0% of a metal Group VIII selected from Fe, Co and Ni provided on a high surface area meso or macroporous support. The the high surface mesoporous support comprises a spheroidal gamma alumina support with a diameter of 1.4 to 2.0 mm, a surface area in the range of from 150 to 220 m2/g, with bimodal narrow pore size distribution, water adsorption capacity in the range of from 1.4 to 2.5 ml/g, gamma crystallinity in the range of 60 to 80% and a bulk density in the range of 0.25 to 0.4 g/ml.

28 Claims, 4 Drawing Sheets

STABLE AND SELECTIVE DEHYDROGENATION CATALYST AND A PROCESS FOR THE PREPARATION THEREOF

FIELD OF THE INVENTION

The present invention relates to a stable and selective dehydrogenation catalyst and a process for its preparation. The novel catalyst formulation of the invention consists of a noble metal component, a group IV A component, a rare earth group component, a group III A component, a group VIII component, an alkali component, a halogen component on an alumina support with a specific pore size distribution. The present invention also relates to a process for the production of unsaturated hydrocarbons from saturated hydrocarbons using the novel catalyst of the invention.

BACKGROUND OF THE INVENTION

Dehydrogenation of saturated hydrocarbons or paraffins specifically C2–C20 paraffins, is an important petrochemical process through which a number of useful unsaturated hydrocarbons are manufactured. These unsaturated hydrocarbons are olefin monomers such as ethylene, propylene butenes, butadiene, styrene and straight chain mono olefins of carbon number range C6–C20, which find extensive applications in the production of variety of plastics, synthetic rubber, detergents and a wide range of chemicals/intermediates of high utility. Furthermore, dehydrogenation of naphthenes and paraffins are the most important reactions during catalytic reforming processes, practiced worldwide for the production of aromatics (BTX) and high octane gasoline.

Dehydrogenation of C10–C16 n-paraffins is a reaction of prime importance particularly to the detergent industry for the manufacture of the active ingredients. The dehydrogenation process comprises of a complex series—parallel reaction network involving primary dehydrogenation, accompanied by a number of side chain reactions, like secondary dehydrogenation, aromatization, isomerisation, cracking and coking. The desired product, n-mono olefin, is formed in the first step, i. e. primary dehydrogenation. Selectivity towards n-mono olefins is of paramount importance in the whole process. An additional drawback of prior art processes is the relatively short catalyst life of 4 to 6 weeks due to active metal sintering and coking.

It is known to suppress accompanying reactions in order to maximise selectivity and increase catalyst life by thermodynamically limiting per pass conversion by the application of pressure and adding one of the reaction products, hydrogen. However, the overall performance in terms of activity, selectivity and stability as exhibited by the catalyst that actually dictate the optimum feasibility of this process. Activity can be defined in terms of per pass conversion as the 'moles of paraffin converted per mole of paraffin fed', the term selectivity as 'moles of n-mono olefin formed per mole of paraffin converted' and the term stability as 'duration for which economically viable activity and selectivity are maintained during the course of the process'. Hence, it is the nature of the support (non-acidic and highly porous), chemical components employed in making the catalyst and the method of preparation of the catalyst composite with unique physico-chemical properties, which enables it to evince these virtues. Hence, catalyst support, catalyst composition as well methods of catalyst preparation are of vital importance.

Prior art catalyst compositions used for the dehydrogenation of paraffins consist primarily of the following metals or their combinations supported on a suitable porous, high surface area support such as gamma $Al_2O_3$.

1. Noble metal (Pt, Re, Pd, Ir, Au, Os)
2. Noble metal+Group IV A metal (Ge, Sn, Pb)
3. Noble metal+Group IV A metal+Group III A metal (Ga, In, Ti)
4. Noble metal+Other Group VIII metals (Fe, Co, Ni) and/or alloys thereof
5. 3 above+Group III A metal or Group III B metal (Sc, Y, La, Ac) as primary active agents, with Group II B metal (Zn, Cd, Hg) as optional secondary activating agent.
6. Noble metal+Group VA metal (As, Sb, Bi) or VI A element (S, Se, Te).
7. 1, 2, 3, 4, 5, or 6 above+Group VII A element (such as halogen in combined form).
8. 1, 2, 3, 4, 5, 6, or 7 above+Group I A metal or Group II A metal such as alkali or alkaline earth metals.
9. Any of 1 to 8 above+sulphur The references to Groups are based on the CAS version of the Periodic Table.

U.S. Pat. Nos. 2,479,109; 2,602,772; 2,930,763; 3,531,543; 3,745,112; 3,632,661; 3,909,451; 3,892,657; 4,329,258; 4,486,574; EP-A -0-183861 D1; 4,786,625; 4,608,360; 3,892,657; 4,197,416; 4,078,743; 3,951,868; 4,136,064; 3,939,059; 4,003,957; 4,025,418; 4,179,405; 5,258,567; 5,358,920; 5,667,260; 5,536,695; 5,849,657; 5,912,394; British Patents 1,499,297; Indian Patents 41667; 128185; 136459; 128349; 140805; 145594; 163412; 163513; 166585; 161974; 179524; 179877; 181623; Chinese Patent CN 87101513A describe the use of catalyst formulations and processes for the preparation with such combination of elements for use in dehydrogenation of saturated normal paraffins.

U.S. Pat. Nos. 2,814,599 and 2,914,464 describe catalysts containing one or more of Ga, In, Sc, Y, La, Ti, and Ac as primary activating agents along with the optional addition of one or more of Hg, Zn or Cd as secondary activating agents for improved reforming activity U.S. Pat. No. 2,930,763 discloses a catalyst composition consisting of Pt 0.1–1.0 weight percent, combined halogen (calculated on elemental basis), 0.1–1.0 weight percent, and alkali metal 0.01–1 weight percent for use in reforming applications in which dehydrogenation is one of the predominant reactions.

U.S. Pat. No. 3,632,661 discloses a catalyst consisting of Pt or Pd 0.1–5% along with Fe 0.01–10% or oxides/alloys thereof as promoters. The catalyst includes optionally Group I B metals as secondary promoters, 0.002–5% or one of Co or Zn 0.1–4% with 0.2–2% weight percent alkali/alkaline earth metals on a near neutral carrier. This method avoids the use of halogenated salts for impregnation and preferably impregnates the promoter prior to the noble metal.

Addition of elements of Group IV A or Group III A are disclosed in the following patents.

U.S. Pat. No. 3,531,543 discloses a catalyst composition for dehydrogenation applications containing Pt, Sn, alkali metal and combined halogen, wherein the alkali metal is added to the support in a first step to yield a support like lithiated Al2O3. The purpose of alkali metal addition is to obtain a relatively neutral support.

U.S. Pat. No. 3,745,112 discloses a catalyst primarily for reforming applications of a similar composition to that disclosed in U.S. Pat. No. 3,531,543 wherein the role of the alkali metal is described as killing of the acidic function of the catalyst. Sn is described as a good promoter.

U.S. Pat. No. 3,909,451 also describes a catalyst of similar composition for dehydrogenation wherein the combined halogen content as calculated on an elemental basis, is less than 0.2 weight percent. Similarly, U.S. Pat. Nos. 4,329,258 and 4,363,721 describe catalysts containing Pt, Sn, and an alkali metal and combined halogen wherein the atomic ratio of alkali metal to Pt is in the range of 0.2 to 10.

U.S. Pat. No. 3,892,657 discloses a catalyst consisting of Pt, In, and one of Ge, Sn, or Pb along with combined halogen, the halogen content calculated on an elemental basis, being variable depending on the application of the catalyst, namely, 0.1 weight percent for dehydrogenation, 3.5 weight percent for reforming and 10 weight percent for isomerisation. In is described as a good promoter when the atomic ratio of In:Pt is 0.1–1:1. A combination of Pt, Sn, In, Cl or Pt and one of Ge, Sn, Pb plus In is described as suitable for reforming reactions while a combination of Pt, In, and alkali or alkaline earth metals is stated to be suitable for dehydrogenation. The combination of Pt, Sn, In, and an alkali/alkaline earth element is not specifically disclosed.

U.S. Pat. No. 3,909,451 teaches the preparation of catalyst composite with platinum, tin and lithium on r-Al2O3 for the function of dehydrogenating of n-paraffins.

U.S. Pat. No. 3,951,868 demonstrates a catalyst composite comprising the support with 0.5wt % of Sn in the form of tin oxide as per the teachings of U.S. Pat. No. 2,620,314, a platinum component, a tin component, an indium component and about 1 wt % of combined chloride for the use specially in catalytic reforming and thereby boosting of a gasoline octane number.

U.S. Pat. No. 4,078,743 relates to catalysts for dehydrogenation of paraffin hydrocarbons to olefins in a medium of hydrogen and to a method of preparing said catalyst. According to this invention catalyst composite comprises a platinum component, an alkali component, and at least on of the three elements i.e. gallium, indium and thallium supported on active alumina.

U.S. Pat. No. 4,136,064 discloses a non-acidic catalyst composite containing a platinum or palladium component, a rhodium component, a Group IV A metal, a cobalt component and an alkali or alkaline earth component with porous carrier for dehydrogenation of dehydrogenatable hydrocarbons.

U.S. Pat. No. 4,197,416 and its family patents 3,939,059; 4,003,957; 4,025,418; 4,179,405 teach a composite comprising non-acidic support with a platinum component, a rhenium component, a cobalt component, a germanium component and an alkali or alkaline earth and particularly for the application of dehydrogenation of dehydrogenatable hydrocarbons.

EP-A-0183861; 4486547 and 4551574 are particularly relevant in part because they teach a catalyst composition comprising a platinum component, a tin component, an indium component, an alkali or alkaline earth component and a porous support material wherein the atomic ratio of indium to platinum group component is more than 1.0. In preferred embodiment, part of the Sn is added at the sol stage and treated in air at 550(C) to result in tin oxide. These preferred embodiments have been considered as prior art catalyst to compare with the present invention.

U.S. Pat. No. 4,608,360 to Abrevaya et al. discloses a combination of a platinum group component, Group IV A (tin) component, Group III A (indium) component, alkali metal component (lithium), a halogen component and optionally a sulphur component and no specific disclosure with respect to the platinum distribution.

U.S. Pat. No. 4,786,625 to Imai et al. for a catalytic composite discloses a catalyst comprising of a platinum group component, a modifier metal component selected from the group consisting of tin, germanium, rhenium component and mixtures thereof; an optional alkali or alkaline earth metal component or mixtures thereof; an optional halogen component and an optional catalytic modifier component on a refractory oxide support having a diameter of at least about 850 microns. The distribution of the platinum component is such that it is surface impregnated, where substantially all of the platinum is located at most within a 400 micron exterior layer and modifier component is uniformly distributed through out the support. The combination of Pt, Sn, In, Li and halogen component is specifically disclosed and as optional well-known modifiers from Group VIII (iron, cobalt or nickel). The patent does not specifically disclose anywhere in the description or the working examples, composites consisting of Pt, Sn, In, Fe, Li and Cl.

Indian patent specification No. 128185 discloses a catalyst consisting of Pt, Ge and an alkali metal or alkaline earth metal on alumina for dehydrogenation applications. Indian patent specification No. 128349 describes a catalyst consisting of Pt, Sn and Ge on an alumina carrier. Indian patent specification No. 140805 discloses the addition of an alkali metal or alkaline earth metal in an amount of from 0.01–5 weight percent to a catalyst of composition described in Indian patent specification No. 128349 and shows the beneficial effect of such addition. The alkali/alkaline earth component is preferably added after impregnation of Pt, Sn and Ge.

Indian patent specification No. 145594 discloses a catalyst composition consisting of Pt 0.2–1%, one of Ga, In, Ti, 0.2–1.0%, an alkali or alkaline earth element 0.2–2 weight percent and combined halogen 0.01 to 0.1 weight percent. This patent shown the superiority of such composition over prior art catalysts consisting of Pt/Al2O3 with alkali or alkaline earth elements with optionally, as or Pb as promoters.

British patent No. 1,499,297 discloses a catalyst similar in composition to that disclosed in Indian Patent No. 145594 for dehydrogenation applications wherein the alkali metal is preferably Li or K, and its atomic ratio in relation to Pt is up to 10 with combined halogen in the range of 0.01 to 0.1 weight percent. Such composition is described in resulting in better selectivity and stability.

Indian patent specification No. 163412 discloses a catalyst with a composition similar to that disclosed in British patent 1,499,297 and Indian Patent No. 145594. However, it claims that combined halogen content greater than 0.2% and an atomic ratio of alkali metal to Pt greater than 10 results in improved activity and selectivity.

Indian patent specification No. 165513 describes a catalytic composition of Pt, one of Group IV A metals selected from Ge, Sn or Pb and an alkali or alkaline earth metal in an amount whereby the atomic ratio of this latter metal to Pt is greater than 10, and the combined halogen content exceeds 0.2 weight percent. Such composition is shown to exhibit better activity and selectivity than prior art catalysts with halogen content of less than 0.2 weight percent.

Indian patent specification No. 161974 discloses a catalyst for dehydrogenation applications consisting of Pt, Sn, In, an alkali or alkaline earth component and combined halogen, wherein the atomic ratio of In:Pt is greater than 1. The support is preferably a Sn—Al2O3 support. The promoting action of In is also disclosed.

U.S. Pat. No. 4,608,360 teaches a catalyst formulation superior to those above for the dehydrogenation of linear paraffins to mono-olefins. The catalyst composite comprises a Group VII, a noble metal component, a co-formed IV A component, an alkali metal or alkaline earth metal component and an alumina support having a surface area of from 5 to 150 m2/g. Additionally, the alumina support is such that less than about 18% of the total pore volume of the support is associated with pores having mean diameter of about 300 Å or less and more than about 55% of the total pore volume of the support is associated with pores having mean diameters of about 600 Å or more. The catalyst formulation in accordance with the above invention consists of 0.38 wt % of Pt, about 0.60 wt % of lithium, about 0.50 wt % of tin and about 1% chlorine. The catalyst had an ABD of about 0.298 g/cc and a surface area of about 80 m2/g and the pore volume distribution was such that 11.8% of the total pore volume of the support was associated with pores having mean diameters of less than about 300 Å or less, and about 60% of the total pore volume of the support was associated with pores having mean diameters of 60 Å or more. IV A metal, tin cogellation are specifically mentioned.

U.S. Pat. No. 5,358,920 discloses a catalyst that comprises a large pore diameter alumina with dual pore size distribution having at least 40% of the total pore volume contributed by pores with pore diameter in the range of 1000–10000 Å and containing sodium as a promoter along with Pt and Sn. The above support is prepared according to the steam treatment of alumina described in Chinese Patent CN 87101513A.

Catalyst formulations with better activity, selectivity and stability than the formulations covered by the patens above have been disclosed in U.S. Pat. No. 5,667,260 which discloses a composition that includes Fe along with Pt, Sn, In, Li and Cl and a process for the preparation thereof.

U.S. Pat. No. 5,536,695 teaches a catalyst formulation containing Pt, Sn, and Li that is prepared (i.e. precursors used and treated) in such a way that it results in x-ray diffraction lines corresponding to lithium aluminate (mainly LiAl5O8) useful for the dehydrogenation of linear paraffins to mono-olefins.

U.S. Pat. No. 5,849,657 and 5,912,394 manifests a catalyst formulation containing Pt, Sn, In and Mg (alkaline earth metal) which is useful for the dehydrogenation of linear paraffins to mono-olefins.

While most of the prior art catalysts show either improved stability, or activity or selectivity, the levels of these parameters are not fully optimised and require improvement.

OBJECTS OF THE INVENTION

It is an object of the invention to provide a novel catalyst formulation useful for the dehydrogenation of saturated hydrocarbons to unsaturated hydrocarbons.

It is another object of the invention to provide a novel catalyst for the dehydrogenation of saturated hydrocarbons to unsaturated hydrocarbons, which has improved stability, activity and selectivity.

It is a further object of the invention to provide a catalyst formulation for the selective dehydrogenation of paraffins.

It is another object of the invention to provide a novel catalyst formulation for the selective dehydrogenation of saturated hydrocarbons to unsaturated hydrocarbons that overcomes the drawbacks of prior art catalysts.

It is a further object of the invention to provide a process for the preparation of the novel catalyst of the invention.

SUMMARY OF THE INVENTION

The novel catalyst composite of the invention has better selectivity, activity and stability than prior art catalyst composites and hence provides better overall performance by yielding more mono-olefins. The present invention relates to a novel catalyst composite consisting of an alumina support, having Sn and Li as acidity attentuators and La as the surface area stabiliser, and active components comprising of platinum component, a tin component, an indium component, an iron component, and a halogen component Cl. The catalysts of the present invention which are different from the prior art in terms of their compositions, and preparation, also show superior performance as compared to the prior art catalysts. The pore size of the catalyst of the present invention are regulated by templating agents like PEG 400/600, or Brij −35 and consists of support modifiers, Sn, La, and Li, and have actice components platinum along with promoters Tin, indium and iron. Particularly, Li and Sn regulate support acidity and lanthanum prevents sintering of the support surface area. In addition, no sulfiding is required to optimise selectivity to mono-olefins. The present invention is an improvement over prior art catalysts, particularly, over U.S. Pat. No. 5,667,260 and EP 0749779.

Accordingly, the present invention provides novel catalyst for use in dehydrogenation of saturated hydrocarbons to unsaturated hydrocarbons, said comprising a composite incorporated within its spatial geometry on a percentage by weight basis, with a uniform concentration gradient, the following active elements:

from 0.1 to 5.0% of a noble metal;

from 0.1 to 5.0% of a metal of Group IV A;

from 0.1 to 6.0% of a metal Group III A;

from 0.1 to 10.0% of an alkali or alkaline earth metal element;

from 0.01 to 10.0% of a halogen; and from 0.1 to 5.0% of a metal Group VIII selected from Fe, Co and Ni provided on a high surface area meso or macroporous support.

Preferably, the support comprises of a spheroidal gamma alumina support with a diameter of 1.4 to 2.0 mm, a surface area in the range of from 150 to 220 m2/g, with bimodal narrow pore size distribution, water adsorption capacity in the range or from 1.4 to 2.5 ml/g, gamma crystallinity in the range of 60 to 80% and a bulk density in the range of 0.25 to 0.4 g/ml.

The present invention provides a process for the preparation of a novel dehydrogenation catalyst useful for the production of unsaturated hydrocarbons from saturated hydrocarbons, said process comprising incorporating active elements comprising i. from 0.01 to 5.0% by weight of a noble metal ii. from 0.1 to 5% by weight of a metal of Group IV A iii. from 0.1 to 6% by weight of a metal of Group III A iv. from 0.1 to 1% by weight of a rare earth v. from 0.1 to 10% by weight of an alkali element vi. from 0.01 to 10% by weight of a halogen; and vii. from 0.1 to 5% of a Group VIII metal selected from Fe, Co and Ni;

within a high surface meso or macroporous support of the kind as described herein to form a composite, drying the composite, and subjecting the dried composite to conventional calcination.

The invention also relates to a process for the preparation of mono-olefins from the corresponding paraffins, said process comprising dehydrogenating said paraffins in any conventional manner in the presence of a novel catalyst comprising a composite incorporated within its spatial geometry on a percentage by weight basis, with a uniform concentration gradient, the following active elements:

from 0.1 to 5.0% of a noble metal;

from 0.1 to 5.0% of a metal of Group IV A;

from 0.1 to 6.0% of a metal Group III A;

from 0.1 to 10.0% of an alkali or alkaline earth metal element;

from 0.01 to 10.0% of a halogen; and from 0.1 to 5.0% of a metal Group VIII selected from Fe, Co and Ni provided on a high surface area meso or macroporous support.

In one embodiment of the invention, the high surface mesoporous support comprises a spheroidal gamma alumina support with a diameter of 1.4 to 2.0 mm, a surface area in the range of from 150 to 220 m2/g, with bimodal narrow pore size distribution, water adsorption capacity in the range of from 1.4 to 2.5 ml/g, gamma crystallinity in the range of 60 to 80% and a bulk density in the range of 0.25 to 0.4 g/ml.

In a further embodiment of the invention, the support has a bulk density of 0.3 g/ml.

In yet another embodiment of the invention, the support comprises 0.1 to 5 wt % of Fe, 0.1 to 5 wt % of Sn and 0.1 to 1 wt % of La.

In a further embodiment of the invention, the support is soaked with surfactants/templates to prevent pore collapse upon drying or calcination and to impart visually improved sphericity.

In yet another embodiment of the invention the active elements incorporated into the high surface area meso or macroporous support comprise platinum as the noble metal, tin as the Group IV A metal, indium as the Group III A metal, Lanthanum as the rare earth element, Lithium as the alkali element, iron as the Group VIII metal and chlorine in combined form as the halogen.

In a further embodiment of the invention, chlorine is present in an amount ranging from 0.05 to 0.1% by weight calculated on an elemental basis and Fe is present in an amount or approximately 0.2% by weight.

In one embodiment of the invention, the active elements are incorporated into the support simultaneously in combination in a single step.

In another embodiment of the invention, the active elements are incorporated into the support stage—wise in any conventional manner.

In a further embodiment of the invention, the active elements are incorporated individually into the support during the preparation of the said support.

In a further embodiment of the invention, the active elements are incorporated into the support by impregnation on the finished support individually or in combination.

In another embodiment of the invention, the active elements may be impregnated on to the finished support either simultaneously or successively in any order.

In yet another embodiment of the invention, the impregnation can be done by any conventional method such as equilibrium adsorption, incipient wetness, spraying, and deposition as a film from the vapour state, coprecipitation, co-gellation or a combination of any of the above methods.

In a further embodiment of the present invention, the tin component is incorporated in two parts during preparation, one part with the alumina sol and the other with the noble metal and promoter elements, and plays a dual role of an acidity attentuator and a promoter.

Preferably, the noble metal, essentially platinum is incorporated into the support simultaneously with the Group IV A metal, essentially tin.

In another embodiment of the invention, part of the Group IV A element and rare earth element are incorporated into the support in a separate step prior to incorporation of the other elements.

In a further embodiment of the invention, part of the Group III A metal is incorporated into the support along with the noble metal.

In a further embodiment of the invention, the alkali or alkaline earth metal is preferably incorporated into the support prior to or simultaneously with the other active elements.

In yet another embodiment of the invention, the active elements are incorporated into the finished support by impregnation employing a solvent, preferably an aqueous solvent, an organic solvent or a mixture thereof, in the presence of anions.

In a further embodiment of the invention, the anions are preferably acidic in nature and are most preferably chloride anions in a concentration range from 0.1 to 15% by weight, preferably 5 to 10% by weight.

In another embodiment of the invention, iron as the Group VIII metal, tin as the Group III A metal and lanthanum as the rare earth element are incorporated into the alumina support at the sol stage of the support preparation or in the first impregnation step.

In one embodiment of the invention, the catalyst composite is preferably dried in a dust free environment at ambient temperature for 1 hour after incorporation therein of the active elements, and thereafter in a flow of purified air at a temperature ranging from 80° C. to 170° C. for 4 to 12 hours.

In another embodiment of the invention, the calcination of the dried catalyst is effected in one or more stages at a temperature in the range from 400° C. to 600° C. for a period of from 4 to 16 hours in an environment of circulating dry air.

In a further embodiment of the invention, the calcined catalyst is subjected to dehalogenation treatment in order to reduce its halogen content.

DETAILED DESCRIPTION OF THE INVENTION

The preparation of the catalyst support of the present invention is different when compared to those described for prior art catalysts, as disclosed in U.S. Pat. No. 2,620,314 and CN 87101513A. In the present invention, pore size distribution is tailored using organic templating agents at the appropriate processing stage. Simple addition of these templates to the alumina sol, as described in prior art (ACS monograph 184, by Chanakya Mishra) does not result in the desired pore size distribution.

Complete accessibility of the active components, located in pores to the reactants, throughout the course of the reaction/process time is highly essential for the realisation of the efficacy of the catalyst. Active components present on micro pores may be accessible initially, but in the course of the reaction, the coke formed could block the micro pore mouth and thus impair the availability of the active sites for further reactions. Therefore, optimum pore size distribution required for complete active metal accessibility to reactants during the course of catalyst life cycle is desired. This optimum pore size distribution should also render required support surface area in order to achieve good platinum dispersion (i.e. lower Pt crystallite size). Thus, tailoring of the pore structure is of prime importance.

Manufacture of the spheroidal alumina support consists of three major steps, preparation of the sol, formation of the solid hydrogel spheres, and further processing to yield the final product.

In the step of formation of the solid hydrogel spheres, an intermediate material consisting of a mixture of alumina sol and the gelling agent, both in the liquid state, are processes to yield hydrogel spheroids of the desired diameter. Conventional oil drop method as disclosed in U.S. Pat. No. 2,620,314 is used for this step.

In the prior art, the solid hydrogel spheres are generally processed through the following steps, oil aging, ammonia aging, washing, drying and calcination to obtain gamma alumina of the desired properties. However, the step of processing is modified in the present invention to obtain alumina support of the desired pore size distribution. In the present invention, hydrogels after aging in oil at 98° C. for 6 hours, aging in 5% aqueous ammonia solution at a temperature of 98 to 100° C. for another 6 hours are converted into pseudo-boehmite spheres. The pseudo-boehmite spheres are then washed with turbulent flow of hot water for 1 hour and allowed to soak in surfactant/templating agent such as PEG–400 (polyethylene glycol) or Brij35 (polyoxyethylene 4 lauryl ether) for 1 hour, followed by draining of the liquid before transferring it for drying. Due to the high boiling point of these templates, they remain in alumina matrix and protect the macro/meso pores from collapsing. On controlled calcination in 5% moisture containing air at 600° C. for 4 hours, pseudo-boehmite spheres are converted into highly meso and macro porous gamma alumina of the present invention.

The present invention results in a novel dehydrogenation catalyst useful for the production of unsaturated hydrocarbons from saturated hydrocarbons, the catalyst comprising i. from 0.1 to 5.0% by weight of a noble metal
  ii. from 0.1 to 5% by weight of a metal of Group IV A
  iii. from 0.1 to 6% by weight of a metal of Group III A
  iv. from 0.1 to 1% by weight of a rare earth
  v. from 0.1 to 10% by weight of an alkali or alkaline earth element
  vi. from 0.01 to 10% by weight of a halogen; and
  vii. from 0.1 to 5% of a Group VIII metal selected from Fe, Co and Ni; incorporated within the spatial geometry of the high surface meso or macroporous support prepared, the proportions of the active elements being in terms of percentage by weight basis.

The active elements incorporated into the support preferably comprise platinum as the noble metal, tin as the Group IV A metal, indium as the Group III A metal, lanthanum as the rare earth element, lithium as the alkali element, iron as the Group VIII metal and chlorine in combined form as the halogen. Chlorine is preferably present in an amount ranging from 0.05 to 0.1% by weight calculated on an elemental basis and Fe is present in an amount or approximately 0.2% by weight.

The tin component may be incorporated in two parts during preparation, one part with the alumina sol and the other with the noble metal and promoter elements, and plays a dual role of an acidity attentuator and a promoter.

The high surface meso or macroporous support comprises a spheroidal gamma alumina support with a diameter of 1.4 to 2.0 mm, a surface area in the range of from 150 to 220 m2/g, with bimodal narrow pore size distribution, water adsorption capacity in the range of from 1.4 to 2.5 ml/g, gamma crystallinity in the range of 60 to 80% and a bulk density in the range of 0.25 to 0.4 g/ml, preferably a bulk density of 0.3 g/ml. Optionally the support may also comprise 0.1 to 5 wt % of Fe, 0.1 to 5 wt % of Sn and 0.1 to 1 wt % of La. The support may if desired be soaked with surfactants/templates to prevent pore collapse upon drying or calcination and to impart visually improved sphericity.

The active elements are incorporated into the support simultaneously in combination in a single step, or support stage-wise in any conventional manner. The active elements may also be incorporated individually or in combination into the support during the preparation of the said support. Alternatively, the active elements are incorporated into the support by impregnation on the finished support individually or in combination. This enables good selectivity in the dehydrogenation of paraffins to the corresponding mono-olefins.

The active elements may be impregnated on to the finished support either simultaneously or successively in any order. The impregnation can be done by any conventional method such as equilibrium adsorption, incipient wetness, spraying, and deposition as a film from the vapour state, coprecipitation, co-gellation or a combination of any of the above methods. The choice of the impregnation procedure will determine the formation of the desired concentration gradient of the active elements within the catalyst composite. The procedure is chosen to result in a composite having a heterogeneous or shell type deposition of elements on the spatial geometry of the support or a homogenous or uniform deposition of the elements therein. The noble metal, metal of Group IV A, metal of Group III A, rare earth metal, alkali or alkaline earth metal and the metal of Group VIII are incorporated into the alumina support by co-precipitation or cogellation during the sol state in the preparation of the support. Alternatively, the metals can also be impregnated into the finished support, simultaneously or successively in any order.

Preferably, the noble metal, essentially platinum is incorporated into the support simultaneously with the Group IV A metal, essentially tin. The precursors for platinum are selected so as to be capable of decomposition on calcination. Preferred platinum precursors include hexachloro platinic acid, platinum acetyl acetonate, tetra-amino platinum nitrate, platinum chloride, etc., for tin the precursors tin (II) chloride dihydrate, tetra butyl tin, tin acetate, tin acetylacetonate, etc, preferably tin (II) chloride dihydrate, for indium the precursors, indium (III) chloride, indium (III) nitrate, indium (III) acetylacetonate, indium acetate etc., preferably indium (III) nitrate, for iron the precursors, iron chloride, iron acetylacetonate, iron nitrate, iron acetate etc., preferably iron(III) nitrate, for lanthanum the precursors, lantanum (III) chloride, lanthanum (III) nitrate, lanthanum acetate, lanthanum (III) acetylacetonate, etc., preferably lanthanum (III) nitrate are used.

Part of the Group IV A metal (Sn) and rare earth element (La) is incorporated into the support in a separate step prior to incorporation of the other elements. Part of the Group IV A metal and the Group III A metal, essentially indium, is incorporated along with the noble metal into the support. The alkali or alkaline earth metal, essentially lithium is preferably incorporated into the support prior to or simultaneously with the other elements.

Incorporation of the active elements into the finished support by impregnation is conveniently effected employing an aqueous solvent, an organic solvent or mixture of the two, in the presence of anions. Such anions are preferably acidic and in particular chloride anions in a concentration range from 0.1% to 15% by weight preferably 5% to 10% by weight. This range is maintained in order to achieve the desired distribution of active elements within the spatial geometry of the support.

The alumina support may be incorporated with iron as the Group VIII metal, tin as the Group IIIA metal and Lanthanum as rare earth element at the sol stage of its preparation or in the first impregnation step.

Preparatory to impregnation, the aqueous and organic solutions employed for the purpose are preferably heated to a temperature of from 40° C. to 70° C. for a maximum of 30 minutes. Thereafter, the solutions are cooled to a temperature in the range of from 5° C. to 40° C. and maintained at this range during the impregnation step. This procedure yields a catalyst with uniform dispersion of elements therein and ensures minimal loss of the impregnated support through mechanical fracture, as a result of the heat of adsorption of the impregnating solution. The quantum of the solution employed for impregnation by the incipient wetness technique ranges from 5% to 30% by weight in excess of the water adsorption capacity of the support, measured according to IS 9700-1981.

After incorporation therein of the active elements, the catalyst composite is preferably dried in a dust-free environment at ambient temperature for 1 hour and thereafter in a flow of purified air at a temperature from 80° C. to 170° C. for 4 to 12 hours.

The calcination of the dried catalyst composite can be effected in one or more stages at a temperature in the range of from 400° C. to 600° C. for a period of from 4 to 16 hours in an environment of circulating dry air.

The calcined catalyst composite of the invention may also be subjected to dehalogenation treatment preferably by employing a counter current steam in order to reduce its halogen content to 0.01% to 5%, preferably 0.05% to 0.1%, by weight. It has been found convenient to dehalogenate the catalyst composite by subjecting it to steaming, employing a 20:80 steam-air mixture at a temperature of from 400 to 550° C. Alternatively, the composite can be dehalogenated by treating it at a temperature, from 10° C. to 80° C., for a period of from 0.5 to 10 hours, with an aqueous solution of a weak base (example 0.5% $NH_4OH$) or salt thereof or with an aqueous solution of an organic or inorganic compound, which undergoes hydrolysis to release such weak base, in the temperature range mentioned. This alternative dehalogenation treatment is the preferred one and the preferred temperature thereof is 40° C. to 80° C. A preferred washing medium for the dehalogenated composite is demineralised water with the washing effected at a temperature of 40° C. to 80° C. for a period of 0.5 to 5 hours. The dehalogenated composite is then dried and further calcined.

Reduction of catalyst composite prior to its use for catalytic dehydrogenation of paraffins is preferably done by subjecting the calcined catalyst to a reduction process by treatment with dry hydrogen+nitrogen mixture of below LEL stream (containing less than 10 ppm by wt. moisture). The reduction is carried out with a GHSV (gas hourly space velocity) of 1000 to 5000 $h^{-1}$ at a temperature range from 300 to 600° C. for a period of 2 to 16 h. Preferable temperature range for reduction is 450–500° C. for 4 h and thereafter, catalytic composite is ready for use in the dehydrogenation of $C_{10}$ to $C_{14}$ n-paraffins.

Yet another feature of the novel catalytic composite and process of its preparation is that upon reduction by preferred method, substantially all the platinum component is reduced to zero oxidation state. The tin and indium components at least 20% of these are in metallic state, the rest being in oxidation states higher than zero. The component lithium, lanthanum and iron are in oxidised state.

The invention will be illustrated in greater detail with reference to the accompanying drawings and examples. In such examples, unless otherwise specified, a chloride content of between 5 to 10 weight percent is maintained in the impregnating solution. The examples are intended to illustrate the invention and should not be considered to restrict the limitations on the broad scope of the invention as set out in the appended claims.

BRIEF DESCRIPTION OF THE ACCOMPANYING DRAWINGS

FIG. 2 is a comparison of catalyst of prior art (Catalyst "C" and "D") and the catalyst of the present invention (catalyst A-1). The effect of temperature on Bromine number under the process conditions of Test 3 are shown.

Table: 1. Exhibits the percentage of paraffins converted versus hours on stream, average selectivity to mono-olefins and average mono-olefin yield (Test-1). (This brings out the superiority of the present invention comparison with prior art).

Table: 2. Bromine Number drop with time data was given for accelerated deactivation test i.e. Test-2b. Shows the stability of the catalyst of present invention in comparison with prior art.

Table: 3. Hydrothermal stability of catalysts of prior art and present invention (Test-4), wherein percent paraffin conversion observed for fresh catalyst and spent catalyst of present invention and prior art has been described. Textural properties were also compared.

For the sake of clarity the illustrations were structured in such a way that first part of it explains the improvements over the invention described in U.S. Pat. No. 5,677,260. The second part of it explains the distinction and superiority of present invention over prior art catalyst, and finally the third part describes the evaluation methods followed.

Part-I

EXAMPLE—I

Preparation of Catalyst Composite of Catalyst—A-1, A-2, A-3, A-4 & A-5

The benefit of including Fe, Sn and La at sol stage in the catalyst formulation with pore size regulated alumina. Pore size regulated spherical alumina support has been used to prepare catalysts of the following composition according to the present invention

| Element/Catalyst | Pt (Wt %) | Fe (Wt %) | Sn (Wt %) | In (Wt %) | La (Wt %) | Li (Wt %) | Cl (Wt %) |
|---|---|---|---|---|---|---|---|
| A-1 | 0.4 | 0.2 | 1.0 | 0.4 | 0.25 | 0.6 | 0.1 |
| A-2 | 0.4 | 0.2 | 1.0 | 0.3 | 0.25 | 0.4 | 0.1 |
| A-3 | 0.4 | 0.2 | 1.0 | 0.4 | NIL | 0.6 | 0.1 |
| A-4 | 0.4 | 0.2 | 0.5 | 0.4 | 0.25 | 0.6 | 0.1 |
| A-5 | 0.4 | 0.2 | 1.0 | 0.3 | 0.25 | 0.6 | 0.1 |

Figure 1:
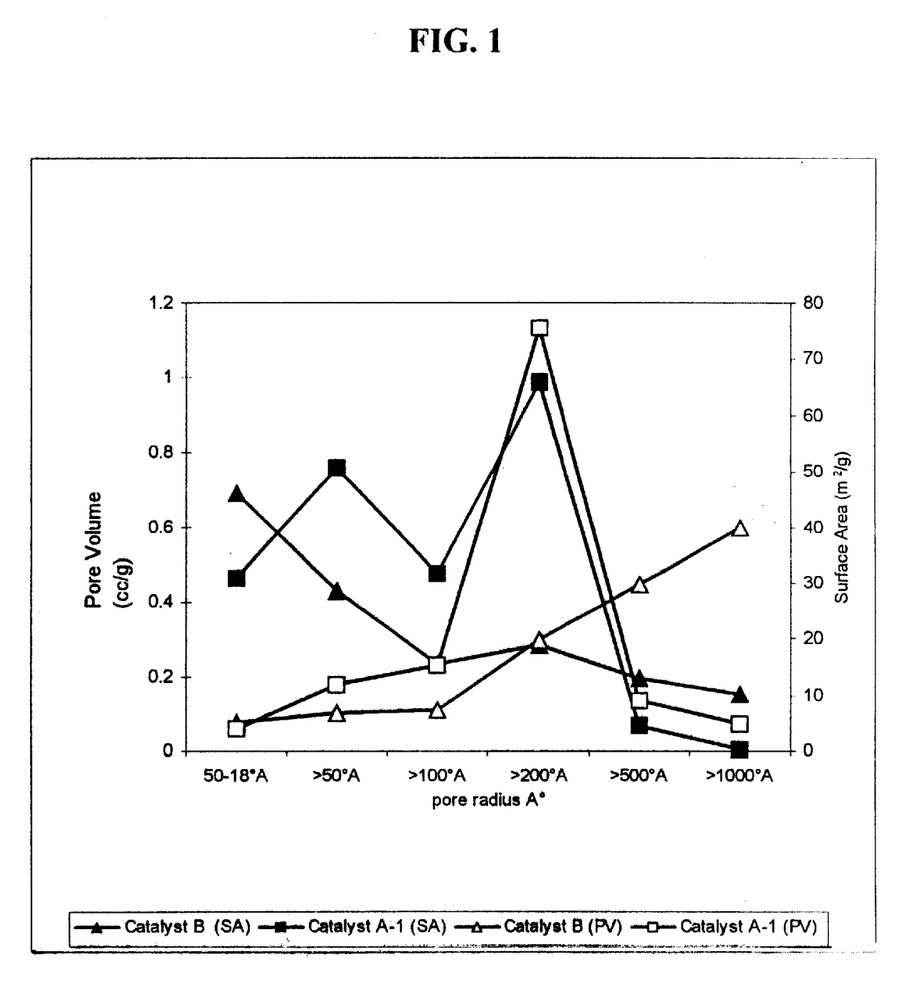
FIG. 1 illustrates the effect of method of support preparation on pore size distribution. The surface area ($m^2/g$) and pore volume (cc/g) contribution plotted against pore radius (Å) of catalyst A-1 and C.

The alumina support employed had a particle diameter distribution in the range of 1.0 mm to 2.0 mm with 65% gamma crystallinity, a BET surface area of 200 m²/g, a water adsorption capacity (WAC) of 1.9 ml/g, with the surface area distribution in various sizes of pores has been described in FIG. 1, a bulk density of 0.29 g/ml, Fe content of 0.2 wt %, Sn content of 0.5 wt % and La content of 0.25 wt %. Fe [NO₃]₃, SnCl₂ 0.6H₂O, and La (NO₃)₃ respectively were used as precursors and were incorporated into the support by adding them to the alumina sol.

On the pre-formed alumina support, as the first step, Li was impregnated using an aqueous solution of LiNO₃, dried and calcined. This support is used for preparing catalyst of preferred embodiment of present invention A-1 and A-2. At this stage a minimum acidity has been observed and the same is manifested by very less activity towards 1-butene isomerisation. This has been studied by using butene-1 isomerisation reaction under identical conditions for all the catalysts. Butene-1 is fed to the reactor at the rate of 6 ml/min along with 60 ml/min helium as diluent and the catalyst bed temperature was maintained at 350° C. In the case of virgin alumina the % conversion was 75 and cis to trans ratio was 0.65, whereas this values for Li impregnated bare alumina was 48% with cis/trans ratio of 0.56 (this support is used for catalyst "C" of prior art). In the case of the support used in the present invention, the butene-1 conversion was 40% with cis to trans ratio of 0.5. For the catalyst D of prior art catalyst considered in our example was having % butene conversion of 60% with 0.7 cis to trans ratio.

Pt, Sn and In were impregnated in a second step with a solution containing H₂PtCl₆, SnCl₂, In[NO₃]₃ and HCl. The above conditions were favourable for the formation of a complex between Pt and Sn. The impregnated support was once again dried and calcined and then subjected to a de-halogenation step in order to reduce the chloride content thereof to 0.1% by weight or less.

In catalyst A-3, the support used was prepared as per the present invention having preferred pore size distribution as shown in FIG. 1, but the difference was that there was no addition of La, at sol stage, only La, Fe and part of Sn was added before forming alumina. In the preparation of A-3, Li was impregnated first followed by drying and calcination. In second impregnation Sn, In and Pt has been co-impregnated onto lithiated alumina. The example A-3 is considered to illustrate the importance of preparation method and composition used in A-1 and A-2.

In catalyst A-4, the support used was prepared as per the present invention having preferred pore size distribution as shown in FIG. 1, but the difference was that there was no addition of "Sn", at sol stage, only La and Fe was added before forming alumina. The contents of A-4, Li was impregnated first followed by drying and calcination. In second impregnation Sn, In and Pt has been co-impregnated onto lithiated alumina. The example A-4 is considered to illustrate the importance of preparation method and composition used in A-1 and A-2.

In catalyst A-5, the support used was prepared as per the present invention having preferred pore size distribution as shown in FIG. 1, but the difference was that there was no addition of "Sn, La and Fe", at sol stage before forming alumina. The contents of A-5, Li was impregnated first followed by drying and calcination. In the second impregnation Sn, La, Fe, In and Pt has been co-impregnated onto lithiated alumina. The example A-5 is considered to illustrate the importance of preparation method and composition used in A-1 and A-2. The performance of formulation E has been presented along with formulation-A for comparison in FIGS. 1 to 4 and tables 1, 2 & 3.

EXAMPLE—II

Preparation of Catalyst Composite of Catalyst—B

The effect of adding Fe, Sn and La to alumina-sol support without pore size regulation. Employing a two-step impregnation of a spheroidal alumina support, a catalyst composite was prepared with the following composition:

| Element | Pt | Fe | Sn | In | La | Li | Cl |
|---|---|---|---|---|---|---|---|
| Wt % | 0.4 | 0.2 | 1.0 | 0.4 | 0.25 | 0.6 | 0.1 |

The alumina support employed had an average particle diameter of 1.85 mm with 68% gamma crystallinity, a BET surface area of 180 m²/g, a water adsorption capacity (WAC) of 1.8 ml/g, with the surface area distribution in various size pores has been described in FIG. 1, a bulk density of 0.29 g/ml, Fe content of 0.2 wt %, Sn content of 0.5 wt % and La content of 0.25 wt. The precursors, Fe [NO₃]₃, SnCl₂ 0.6H₂O, and La (NO₃)₃ were incorporated into the support at the sol stage in its preparation.

In the first step of impregnation, a solution of LiNO₃ was employed to impregnate the support thereafter the support thus impregnated was dried and calcined. Pt, Sn and In were impregnated in a second step with solution containing H₂PtCl₆, SnCl₂, In[NO₃]₃ and HCl. The re-impregnated support was once again dried and calcined and then subjected to a de-halogenation step in order to reduce the chlorine content thereof to 0.07% by weight.

The performance of formulation E has been presented along with formulation-A for comparison in FIGS. 1 to 4 and tables 1, 2 & 3.

EXAMPLE—III

Preparation of Catalyst Composite of Catalyst—C

The catalyst formulation as per the U.S. Pat. No. 5,677,260.

Employing a two-step impregnation of a spheroidal alumina support, a catalyst composite according to U.S. Pat. No. 5,677,260 was prepared, with the following composition by weight:

| Element | Pt | Fe | Sn | In | Li | Cl |
|---|---|---|---|---|---|---|
| Wt % | 0.4 | 0.2 | 0.5 | 0.4 | 0.6 | 0.1 |

The alumina support employed had an average particle diameter of 1.85 mm with 75% gamma crystallinity, a BET surface area of 170 m$^2$/g, a water adsorption capacity (WAC) of 1.8 ml/g, mesoporous distribution of pores, a bulk density of 0.31 g/ml, and a Fe content of 0.2 wt. % as a solution of Fe [NO$_3$]$_3$ which was incorporated into the support at the sol stage in its preparation.

In the first step of impregnation, a solution of LiNO$_3$ was employed to impregnate the support thereafter the support thus impregnated was dried and calcined. Pt, Sn and In were co-impregnated in a second step using a solution containing H$_2$PtCl$_6$, SnCl$_2$, In[NO$_3$]$_3$ and HCl. The re-impregnated support was once again dried and calcined and then subjected to a de-halogenation step in order to reduce the chlorine content thereof to 0.07% by weight. The performance of formulation E has been presented along with formulation-A for comparison in FIGS. 2 to 4 and tables 1, 2 & 3.

Part-II

EXAMPLE—IV

Comparative

Preparation of Catalyst Composite of Catalyst—D as per the U.S. Pat. No. 4,608,360

| Element | Pt | Sn | In | Li |
|---|---|---|---|---|
| Wt % | 0.40 | 0.45 | 0.31 | 0.45 |

Catalyst D with the above composition was prepared as per the teachings of U.S. Pat. No. 4,608,360. The results are presented in FIGS. 2 to 6. It is clear that the present invention Catalyst A is superior with respect to activity, selectivity and stability (life) of the catalyst described in Catalyst D.

EXAMPLE—V

Preparation of Catalyst Composite of Catalyst—E

| Element | Pt | Sn | In | Li | S |
|---|---|---|---|---|---|
| Wt % | 0.415 | 0.5 | 0.39 | 0.6 | 0.1 |

Formulation E was prepared as per the prior art teachings of the above patents EP-A-0183861, 4486547 and 4551574 preferred embodiment. In preferred embodiment, part of the Sn was added to the alumina sol and treated in air at 550° C. to result in tin oxide.

Figure 3:
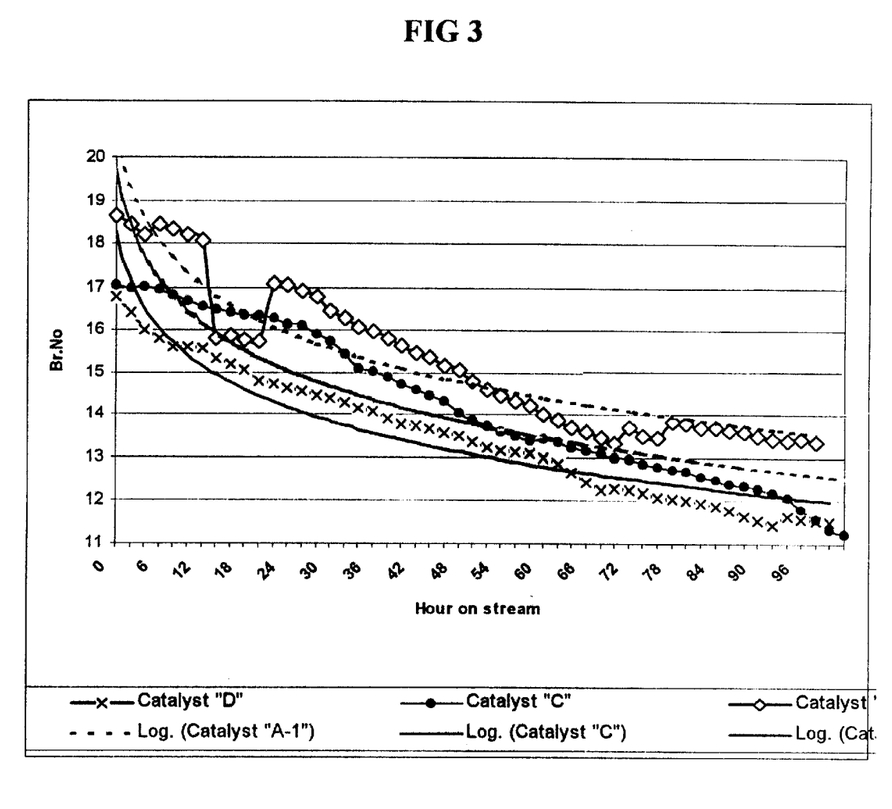
FIG. 3 shows the bromine number variation with time on stream and is a high severity catalyst evaluation (Isothermal test, i.e. Test 2-a) on the catalyst of the present invention (catalyst A-1) and some prior art catalysts (catalysts "C" and "D").
Figure 4:
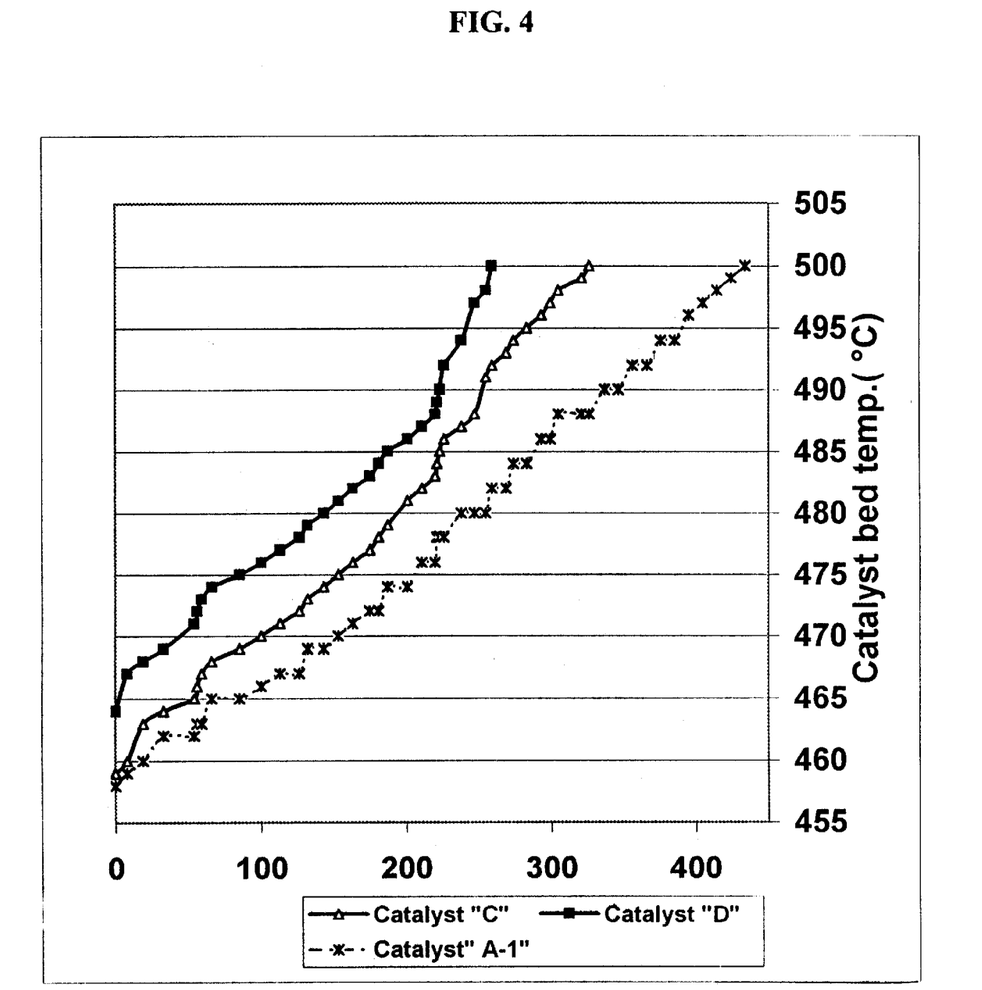
FIG. 4 illustrates the evaluation of catalysts under conditions proposed in Iso-conversional test i.e. Test 3 wherein the reactor temperature versus hour on stream are plotted for catalyst of the invention (catalyst A-1) and some prior art catalysts (catalysts "C" and "D").

The performance of formulation E has been presented along with formulation-A for comparison in FIGS. 2 to 4 and tables 1, 2 & 3.

EXAMPLE—VI

Preparation of Catalyst Composite of Catalyst—F

The catalyst—F was prepared according to the method set forth in U.S. Pat. No. 4,786,625 (Imai). This is specifically relevant due to some of its similarities in composition but is different than that of present invention.

| Element | Pt | Sn | Li |
|---|---|---|---|
| Wt % | 0.42 | 2.7 | 0.6 |

To produce this catalyst of this example, support, a spheroidal alumina having a diameter of around 1500 microns was prepared from tin containing hydrosol by using well known oil drop method. The rest of the procedure adopted was as described in Example 2 of the above patent. The performance of formulation F has been presented along with formulation-A for comparison in FIGS. 2 to 4 and tables 1, 2 & 3.

EXAMPLE—VII

Preparation of Prior Art Catalyst Composite of Catalyst—G

| Element | Pt | Sn | Na |
|---|---|---|---|
| Wt % | 0.41 | 0.748 | 0.55 |

Prior art catalyst with the composition above was prepared as described in catalyst (I) of example in U.S. Pat. No. 5,358,920. That consists of a large pore diameter alumina with dual pore size distribution having at least 40% of the total pore volume contributed by pores with pore diameter in the range of 1000–10000 A° and containing sodium as promoter along with Pt & Sn. The above support was prepared by steam treatment of alumina as described in CN 87101513A. The performance of formulation G has been presented along with formulation-A for comparison in FIGS. 2 to 4 and tables 1, 2 & 3.

EXAMPLE—VIII

Preparation of Prior Art Catalyst Composite (Catalyst—H)

| Element | Pt | Sn | In |
|---|---|---|---|
| Wt % | 0.31 | 0.80 | 0.71 |

U.S. Pat. No. 5,536,695 teaches a catalyst formulation containing Pt, Sn and Li and it was prepared (i.e. precursors used and treated) in such a way that lithium aluminate (mainly $LiAl_5O_8$) phase, as revealed by x-ray diffraction lines, is formed. Catalyst H was prepared as per the teachings of the above patent, in specific as in the catalyst B of example 2. The performance of formulation H has been presented along with formulation-A for comparison in FIGS. 2 to 4 and tables 1, 2 & 3.

EXAMPLE—IX

Preparation of Catalyst Composite of Catalyst—I

| Element | Pt | Sn | In | Mg |
| --- | --- | --- | --- | --- |
| Wt % | 0.415 | 0.5 | 0.39 | 0.6 |

U.S. Pat. Nos. 5,849,657 and 5,912,394 manifests a catalyst formulation containing Pt, Sn, In and Mg (alkaline earth metal) which is useful for the dehydrogenation of linear paraffins to mono-olefins. The catalyst composite Catalyst—I was in accordance with the catalyst C of example 2 of the above patent. The performance of formulation I has been presented along with formulation-A for comparison in FIGS. 2 to 4 and tables 1, 2 & 3.

EXAMPLE—X

Preparation of Catalyst Composite of Catalyst—J

The importance of addition of Pt and Sn together.

Catalyst of composition similar to that in Example I, Catalyst A-1, was prepared by a different method of impregnation, wherein Fe, La and total Sn was incorporated in alumina sol, then Li was impregnated onto the alumina support using an aqueous solution of $LiNO_3$, followed by drying and calcination. Pt and In were impregnated together in a second step. The catalyst was then dried and calcined. It was then subjected to a dehalogenation step and the Cl content reduced to 0.08 wt %.

The results of evaluation of this catalyst formulation vis a vis Catalyst A showed that the initial activities of both catalysts were identical but Catalyst J tends to deactivate rapidly due to coking and agglomeration of platinum [fall in activity is about 1.25 times that of Catalyst A]. The results show that incorporation of all Sn content in one step, prior to incorporation of Pt results in relatively poor stability.

Certain catalyst formulations prepared according to the present invention were tested for their activity, stability and selectivity for dehydrogenation of $C_{10}$–$C_{13}$ n-paraffins under the reaction conditions described hereafter. All experimental tests were performed in a once-through, tubular, axial flow, packed bed reactor operated at near isothermal conditions. The catalysts were pre-reduced in a stream of hydrogen at 470° C. for 2 hours in all the cases. The performance of formulations of prior art has been presented along with formulation A-1 and A-2 of present invention for comparison in FIGS. 2 to 4 and tables 1, 2 & 3.

Part-III

EXAMPLE—XI

Performance Evaluation Tests

Various types of tests were carried out as described below, to establish superior catalyst formulation in terms of activity, selectivity, stability and mono-olefins yield:

Isothermal Tests: (Test-1) Monitoring of conversion of the paraffins under near isothermal reaction conditions, with the following process conditions:

| LHSV | $30\ h^{-1}$ |
| --- | --- |
| Temperature | 450° C. |
| Pressure | Atmospheric. |
| $H_2$:HC (mol/mol) | 6. |
| Feed | n-Decane |

Reactant and product streams, consisting of paraffins, mono olefins, diolefins and aromatics were analysed using HPLC fitted with micronised silica column and Gas chromatograph fitted with Carbowax20M, 50 mtrs capillary column.

Isothermal Tests: (Test-2a) Monitoring of conversion of the paraffins under near isothermal reaction conditions and following process conditions:

| LHSV | $25\ h^{-1}$ |
| --- | --- |
| Temperature | 485° C. |
| Pressure | 20 psig |
| $H_2$:HC (mol/mol) | 6. |
| Feed | |

| $C_{10}$ | 20.36 |
| --- | --- |
| $C_{11}$ | 26.50 |
| $C_{12}$ | 28.08 |
| $C_{13}$ | 21.74 |

$C_9$ and $C_{14}$ are in traces.

High severity Isothermal Tests: (Test-2b) Monitoring of conversion of the paraffins under near isothermal reaction conditions. Specifically, the result resonate the effect of pore size distribution on catalyst stability. The reaction conditions were:

| LHSV | $25\ h^{-1}$ |
| --- | --- |
| Temperature | 480° C. |
| Pressure | atmospheric |
| $H_2$:HC (mol/mol) | 2 |
| Feed | It as in Test 2a. |

Iso-conversional Tests: (Test-3) Monitoring of the reactor temperature required for maintaining a constant per pass paraffin conversion viz. 13% with the following process conditions:

| LHSV | $20\ h^{-1}$ |
| --- | --- |
| Pressure | 1.38 bar (20 psi). |
| $H_2$:HC (mol/mol) | 6. |
| Conversion level | 13 ± 0.5%. |

As stated earlier, "conversion" is defined as "the moles of paraffin converted per mole of paraffin fed" and "selectivity" is defined as "the moles of mono-olefins formed per mole of paraffin converted across the reactor".

Hydrothermal sintering test (Test-4): (stability or stability against sintering)

Pre-reduced catalysts under comparison are subjected to identical process conditions i.e., temperature, hydrogen flow and moisture. Temperature and moisture in the hydrogen promote sintering of active centres of the catalyst thereby reduce the specific metal surface available for reaction. The conditions used for hydrothermal stability test are as follows:

| | |
|---|---|
| Temperature | 485° C. |
| Pressure | Atmospheric |
| H₂(ml/min) | 50. |
| H₂O | 5000 ppm in H₂ |
| Time (hours) | 100 |

After the above treatment the catalysts are removed evaluated as described in Test-1. The results observed are tabulated in table:2.

All the comparisons were made under identical process conditions. The scope of the invention is not restricted only to the examples which are merely illustrative.

TABLE 1

| Catalyst | Hour on stream (Bromine Number) 1 | 10 | Relative Stability | Average Paraffin Conv. (10 h.) | Average Selectivity to MO | Average Selectivity to Total Olefins | Average Selectivity to Di-Olefins | Av. Yield | % yield |
|---|---|---|---|---|---|---|---|---|---|
| A-1 | 19.52 | 18.4 | 0.95 | 18.78 | 89.78 | 97.48 | 7.69 | 16.93 | 118 |
| A-2 | 17.86 | 17.26 | 0.96 | 17.55 | 90.67 | 97.71 | 7.04 | 15.91 | 111 |
| A-3 | 16.12 | 15.49 | 0.96 | 15.62 | 89.96 | 97.04 | 7.08 | 14.05 | 98 |
| A-4 | 18.26 | 16.49 | 0.92 | 17.32 | 90.02 | 97.68 | 7.65 | 15.59 | 108 |
| A-5 | 17.75 | 16.54 | .93 | 16.92 | 90.6 | 97.84 | 7.24 | 15.33 | 107 |
| B | 18.86 | 16.31 | 0.89 | 17.40 | 86.55 | 95.24 | 8.69 | 15.06 | 105 |
| C | 18.37 | 15.69 | 0.86 | 16.60 | 86.62 | 96.20 | 9.58 | 14.38 | 100 |
| D | 17.19 | 13.85 | 0.82 | 14.98 | 86.47 | 95.49 | 9.02 | 12.95 | 90 |
| E | 16.96 | 14.33 | 0.84 | 15.40 | 87.90 | 97.01 | 9.11 | 13.54 | 94 |
| F | 11.19 | 9.25 | 0.83 | 9.61 | 87.25 | 98.65 | 11.40 | 8.38 | 58 |
| G | 14.21 | 11.38 | 0.81 | 12.24 | 87.41 | 96.79 | 9.38 | 10.70 | 74 |

TABLE 2

| HOS/ Catalyst | A-1 | A-2 | A-3 | A-4 | A-5 | B | C | D | E | F | G | H | I | J |
|---|---|---|---|---|---|---|---|---|---|---|---|---|---|---|
| 0.17 | 27.21 | 26.93 | 21.63 | 17.75 | 30.2 | 18.11 | 21.63 | 17.33 | 19.4 | 15.11 | 19.37 | 19.5 | 14.49 | 17.8 |
| 0.33 | 22.45 | 23.03 | 17.35 | 15.53 | 27.19 | 14.98 | 18.3 | 15.53 | 17.48 | 11.01 | 18.6 | 18.1 | 13.71 | 16.2 |
| 0.50 | 19.7 | 19.98 | 15.3 | 13.7 | 24.66 | 13.32 | 16.71 | 15.26 | 16.39 | 9.72 | 17.73 | 17.1 | 13.39 | 14.2 |
| 1.00 | 16.21 | 17.18 | 12.48 | 11.61 | 20.88 | 11.62 | 15.05 | 13.39 | 14.56 | 8.49 | 16.71 | 15.8 | 12.54 | 13.4 |
| 1.50 | 14.09 | 14.76 | 10.3 | 10.38 | 18.93 | 10.1 | 13.47 | 12.4 | 12.98 | 7.55 | 15.03 | 14.2 | 11.72 | 11.2 |
| 2.00 | 12.37 | 13.85 | 10.17 | 9.73 | 17.58 | 9.49 | 12.53 | 11.06 | 11.41 | 7.27 | 14.18 | 13.6 | 11.13 | 9.6 |
| 3.00 | 11.14 | 13.16 | 8.95 | 9.12 | 15.92 | 8.48 | 11.52 | 10.32 | 10 | 6.49 | 12.74 | 11.5 | 10.39 | 8.2 |
| 4.00 | 10.09 | 12.13 | 8.41 | 8.37 | 14.55 | 7.65 | 10.28 | 9.39 | 9.44 | 5.99 | 11.7 | 9.8 | 9.55 | 7.5 |
| 5.00 | 9.47 | 11.48 | 8.25 | 8.01 | 13.16 | 7.0 | 9.32 | 8.38 | 9.02 | 5.58 | 11.01 | 8.2 | 9.05 | 6.8 |

TABLE 3

| Example | Activity (Bromine number) Fresh | Sintered | % deactivation from fresh | Surface area (m²/g) Fresh | Sintered | % deactivation from fresh |
|---|---|---|---|---|---|---|
| Catalyst "C" | 19.07 | 15.9 | 16.6 | 183 | 143 | 22 |
| Catalyst "A-1" | 18.59 | 15.49 | 16.7 | 200 | 192 | 4 |
| Catalyst "A-2" | 19.3 | 15.64 | 19.0 | 200 | 190 | 5 |
| Catalyst "D" | 16.87 | 14.68 | 13.0 | 173 | 138 | 20 |
| Catalyst "J" | 19.1 | 10 | 48.0 | 198 | 180 | 9 |
| Catalyst "G" | 14.21 | 13 | 8.5 | 135 | 134 | 1 |

We claim:

1. A catalyst for use in the dehydrogenation of saturated hydrocarbons to unsaturated hydrocarbons, said catalyst comprising the following active elements incorporated within its spatial geometry on a percentage by weight basis:
   i. from 0.1 to 5.0% of a noble metal;
   ii. from 0.1 to 5% of a metal of Group IV A;
   iii. from 0.1 to 6% of a metal of Group III A;
   iv. from 0.1 to 1% of a rare earth metal;
   v. from 0.1 to 10% of an alkali or an alkaline earth element;
   vi. from 0.01 to 10% of a halogen; and
   vii. from 0.1 to 5% of a Group VIII metal selected from Fe, Co and Ni; provided on alumina mesoporous or macroporous support having a high surface area.

2. A catalyst as claimed in claim 1 wherein the active elements comprise platinum as the noble metal, tin as the Group IV A metal, indium as the Group III A metal, Lanthanum as the rare earth element, Lithium as the alkali element, iron as the Group VIII metal and chlorine in combined form as the halogen.

3. A catalyst as claimed in claim 1 wherein the mesoporous or macroporous support comprises a spheroidal gamma alumina support with a diameter of 1.4 to 2.0 mm, a surface area in the range of from 150 to 220 m²/g, with bimodal narrow pore size distribution, water adsorption capacity in the range of from 1.4 to 2.5 ml/g, gamma crystallinity in the range of 60 to 80% and a bulk density in the range of 0.25 to 0.4 g/ml, with 60 to 80% of its surface area contribution being from said mesoporous or macroporous pores.

4. A process for the preparation of a catalyst for use in the dehydrogenation of saturated hydrocarbons to unsaturated hydrocarbons, said process comprising the steps of:
   a) incorporating within its spatial geometry on a percentage by weight basis, active elements comprising:

i. from 0.1 to 5.0% of a noble metal;
ii. from 0.1 to 5% of a metal of Group IV A;
iii. from 0.1 to 6% of a metal of Group III A;
iv. from 0.1 to 1% of a rare earth metal;
v. from 0.1 to 10% of an alkali or an alkaline earth metal element;
vi. from 0.01 to 10% of a halogen; and
vii. from 0.1 to 5% of a Group VIII metal selected from Fe, Co and Ni; within an alumina mesoporous or macroporous support having a high surface area comprising a spheroidal gamma alumina support with a diameter of 1.4 to 2.0 mm, a surface area in the range of from 150 to 220 m²/g, with bimodal narrow pore size distribution, water adsorption capacity in the range of from 1.4 to 2.5 ml/g, gamma crystallinity in the range of 60 to 80% and a bulk density in the range of 0.25 to 0.4 g/ml, to form a composite; b) drying the composite to form a dried composite; and c) subjecting the dried composite to calcination to obtain the catalyst.

5. A process as claimed in claim 4 wherein the active elements comprise platinum as the noble metal, tin as the Group IV A metal, indium as the Group III A metal, lanthanum as the rare earth metal, lithium as the alkali element, iron as the Group VIII metal and chlorine in combined form as the halogen.

6. A process as claimed in claim 4 wherein the active elements are incorporated into the mesoporous or macroporous support by impregnation employing a solvent selected from an aqueous solvent, an organic solvent or a mixture thereof, in the presence of anions.

7. A process as claimed in claim 6 wherein the anions are acidic in nature.

8. A process as claimed in claim 4, wherein the calcination of the catalyst is effected in one or more stages at a temperature in the range from 400° C. to 600° C. for a period of from 4 to 16 hours in an environment of circulating dry air.

9. A catalyst as claimed in claim 2 wherein the mesoporous or macroporous support comprises a spheroidal gamma alumina support with a diameter of 1.4 to 2.0 mm, a surface area in the range of from 150 to 220 m²/g, with bimodal narrow pore size distribution, water adsorption capacity in the range of from 1.4 to 2.5 ml/g, gamma crystallinity in the range of 60 to 80% and a bulk density in the range of 0.25 to 0.4 g/ml, with 60 to 80% of its surface area contribution being from mesoporous or macroporous pores.

10. A process as claimed in claim 7 wherein the anions are chloride anions in a concentration of from 0.1 to 15% by weight of the alumina support.

11. A process as claimed in claim 10 wherein the concentration of chloride anions are present in a concentration of from 5 to 10% by weight of the alumina support.

12. A process for the preparation of a catalyst for use in the dehydrogenation of saturated hydrocarbons to unsaturated hydrocarbons, said process comprising the steps of:
    a) incorporating within its spatial geometry on a percentage by weight basis, active elements comprising:
       i. from 0.1 to 5.0% of a noble metal;
       ii. from 0.1 to 5% of a metal of Group IV A;
       iii. from 0.1 to 6% of a metal of Group III A;
       iv. from 0.1 to 1% of a rare earth metal;
       v. from 0.1 to 10% of an alkali or an alkaline earth metal;
       vi. from 0.01 to 10% of a halogen; and
       vii. from 0.1 to 5% of a Group VIII metal selected from Fe, Co and Ni; within an alumina mesoporous or macroporous support having a high surface area comprising a spheroidal gamma alumina support with a diameter of 1.4 to 2.0 mm, a surface area in the range of from 150 to 220 m²/g, with bimodal narrow pore size distribution, water adsorption capacity in the range of from 1.4 to 2.5 ml/g, gamma crystallinity in the range of 60 to 80% and a bulk density in the range of 0.25 to 0.4 g/ml, to form a composite;
    b) drying the composite to form a dried composite;
    c) subjecting the dried composite to calcination to form a calcined composite; and
    d) subjecting further the calcined composite to steaming with a 20:80 steam-air mixture at a temperature of from 400 to 550° C. to decrease the halogen content to 0.07 to 0.1% by weight.

13. A process as claimed in claim 12 wherein the active elements comprise platinum as the noble metal, tin as the Group IV A metal, indium as the Group III A metal, lanthanum as the rare earth metal, lithium as the alkali element, iron as the Group VIII metal and chlorine in combined form as the halogen.

14. A process as claimed in claim 12 wherein the active elements are incorporated into the finished support by impregnation employing a solvent selected from an aqueous solvent, an organic solvent or a mixture thereof in the presence of anions.

15. A process as claimed in claim 14 wherein the anions are acidic in nature.

16. A process as claimed in claim 12 wherein the calcination of the dried catalyst is effected in one or more stages at a temperature in the range from 400° C. to 600° C. for a period of from 4 to 16 hours in an environment of circulating dry air.

17. A process as claimed in claim 12 wherein the anions are chloride anions in a concentration of from 0.1 to 15% by weight of the alumina support.

18. A process as claimed in claim 17 wherein the concentration of chloride anions are present in a concentration of from 5 to 10% by weight of the alumina support.

19. A process for the preparation of a catalyst for use in the dehydrogenation of saturated hydrocarbons to unsaturated hydrocarbons, said process comprising the steps of:
    a) incorporating within its spatial geometry on a percentage by weight basis, active elements comprising:
       i. from 0.1 to 5.0% of a noble metal;
       ii. from 0.1 to 5% of a metal of Group IV A;
       iii. from 0.1 to 6% of a metal of Group III A;
       iv. from 0.1 to 1% of a rare earth metal;
       v. from 0.1 to 10% of an alkali or an alkaline earth metal;
       vi. from 0.01 to 10% of a halogen; and
       vii. from 0.1 to 5% of a Group VIII metal selected from Fe, Co and Ni; within an alumina mesoporous or macroporous support having a high surface area comprising a spheroidal gamma alumina support with a diameter of 1.4 to 2.0 mm, a surface area in the range of from 150 to 220 m²/g, with bimodal narrow pore size distribution, water adsorption capacity in the range of from 1.4 to 2.5 ml/g, gamma crystallinity in the range of 60 to 80% and a bulk density in the range of 0.25 to 0.4 g/ml, to form a composite;
    b) drying the composite to form a dried composite;
    c) subjecting the dried composite to calcination; and
    d) subjecting further the calcined composite to treatment at a temperature in the range of from 10° C. to 80° C., for a period of from 0.5 to 10 hours, with an aqueous solution of an organic or inorganic compound, which undergoes hydrolysis to release sufficient base in said temperature range, to decrease the halogen content to 0.07 to 1.0% by weight.

20. A process as claimed in claim 19 wherein the active elements comprise platinum as the noble metal, tin as the group IV A metal, indium as the Group III A metal, lanthanum as the rare earth metal, lithium as the alkali metal, iron as the Group VIII metal and chlorine in combined form as the halogen.

21. A process as claimed in claim 19 wherein the active elements are incorporated into the finished support by impregnation employing a solvent selected from an aqueous solvent, an organic solvent and a mixture thereof in the presence of anions.

22. A process as claimed in claim 21 wherein the anions are acidic in nature.

23. A process as claimed in claim 19 wherein the calcination of the dried composite is effected in one or more stages at a temperature in the range from 400° C. to 600° C. for a period of from 4 to 16 hours in an environment of circulating dry air.

24. A process as claimed in claim 22 wherein the anions are chloride anions in a concentration of from 0.1 to 15% by weight of the alumina support.

25. A process as claimed in claim 19 wherein the concentration of chloride anions are present in a concentration of from 5 to 10% by weight of the alumina support.

26. A process as claimed in claim 19 wherein the base is selected from 0.5% $NH_4OH$ and salts thereof.

27. The process as claimed in claim 12 wherein the mesoporous or macroporous support comprises a spheroidal gamma alumina support with a diameter of 1.4 to 2.0 mm, a surface area in the range of from 150 to 220 $m^2/g$, with bimodal narrow pore size distribution, water adsorption capacity in the range of from 1.4 to 2.5 ml/g, gamma crystallinity in the range of 60 to 80% and a bulk density in the range of 0.25 to 0.4 g/ml, with 60 to 80% of its surface area contribution being from mesoporous or macroporous pores.

28. The process as claimed in claim 19 wherein the mesoporous or macroporous support comprises a spheroidal gamma alumina support with a diameter of 1.4 to 2.0 mm, a surface area in the range of from 150 to 220 $m^2/g$, with bimodal narrow pore size distribution, water adsorption capacity in the range of from 1.4 to 2.5 ml/g, gamma crystallinity in the range of 60 to 80% and a bulk density in the range of 0.25 to 0.4 g/ml, with 60 to 80% of its surface area contribution being from mesoporous or macroporous pores.

* * * * *